US 9,127,242 B2

(12) United States Patent
Guertin et al.

(10) Patent No.: US 9,127,242 B2
(45) Date of Patent: Sep. 8, 2015

(54) TISSUE AND ORGAN GRAFT BIOREACTOR AND METHOD OF OPERATION

(76) Inventors: Patrick M. Guertin, Mendon, MA (US); Parrish M. Galliher, Littleton, MA (US); Michael Fisher, Ashland, MA (US); Joseph D. Crowell, S. Hamilton, MA (US); Colin R. Tuohey, Medway, MA (US); Laura A. Niklason, Greenwich, CT (US); William E. Tente, Seekonk, MA (US); Shannon M. Dahl, Durham, NC (US); Juliana Blum, Wake Forest, NC (US); Justin Strader, Cary, NC (US)

( * ) Notice: Subject to any disclaimer, the term of this patent is extended or adjusted under 35 U.S.C. 154(b) by 0 days.

(21) Appl. No.: 13/262,155

(22) PCT Filed: Apr. 5, 2010

(86) PCT No.: PCT/US2010/029942
§ 371 (c)(1),
(2), (4) Date: Sep. 29, 2011

(87) PCT Pub. No.: WO2010/115185
PCT Pub. Date: Oct. 7, 2010

(65) Prior Publication Data
US 2012/0028234 A1 Feb. 2, 2012

Related U.S. Application Data

(60) Provisional application No. 61/166,567, filed on Apr. 3, 2009, provisional application No. 61/166,585, filed on Apr. 3, 2009.

(51) Int. Cl.
*C12M 1/00* (2006.01)
*C12M 3/00* (2006.01)
(Continued)

(52) U.S. Cl.
CPC ............... *C12M 27/00* (2013.01); *C12M 21/08* (2013.01); *C12M 23/14* (2013.01); *C12M 23/28* (2013.01); *C12M 25/14* (2013.01); *C12M 29/06* (2013.01)

(58) Field of Classification Search
CPC ... A01N 1/0247; A01N 1/0242; C12M 23/14; C12M 23/28; C12M 21/08
See application file for complete search history.

(56) References Cited

U.S. PATENT DOCUMENTS 6,379,956 B1 * 4/2002 Bader ........................... 435/325
6,416,995 B1 * 7/2002 Wolfinbarger ............. 435/289.1
(Continued)

FOREIGN PATENT DOCUMENTS

JP 2003-265164 9/2003

OTHER PUBLICATIONS

International Search Report and Written Opinion, dated May 18, 2010, for PCT/US2010/029942 (the parent case), 9 pages (in English).

(Continued)

*Primary Examiner* — Nathan Bowers
(74) *Attorney, Agent, or Firm* — Ziegler IP Law Group, LLC

(57) ABSTRACT

A single-use, single or multiple tissue, organ, and graft bioreactor and environmental control system is designed to replicate the necessary conditions for growth of tissues, organs, or grafts, while addressing problems in scaling up the tissue growth; adaptation to a single-use or disposable format; and operation as a stand-alone unit that provides full environmental control of cell culture conditions.

14 Claims, 6 Drawing Sheets

(51) Int. Cl.
*A01N 1/00* (2006.01)
*C12M 1/02* (2006.01)
*C12M 1/12* (2006.01)

(56) References Cited

U.S. PATENT DOCUMENTS 7,033,823 B2  4/2006  Chang
2004/0219659 A1*  11/2004  Altman et al. ............. 435/284.1
2005/0147958 A1*  7/2005  Hassanein et al. ............. 435/1.1
2008/0213894 A1  9/2008  Antwiler ................. C12N 5/00
2008/0234806 A1*  9/2008  Dancu .......................... 623/1.41
2009/0035856 A1  2/2009  Galliher et al. .......... C12N 5/06

OTHER PUBLICATIONS

Extended European Search Report received for European Patent Application No. EP10759533.2, dated Apr. 8, 2015, 7 pages.

* cited by examiner

TISSUE AND ORGAN GRAFT BIOREACTOR AND METHOD OF OPERATION

RELATED APPLICATIONS

This application claims the benefit under 35 USC 119(e) of U.S. Provisional Application No. 61/166,567, filed on Apr. 3, 2009 and U.S. Provisional Application No. 61/166,585, filed on Apr. 3, 2009, both of which are incorporated herein by this reference in their entireties.

STATEMENT OF GOVERNMENT INTEREST

This invention was made with Government support under 1R43DK085760-01 awarded by the National Institute of Diabetes and Digestive and Kidney Diseases, National Institutes of Health. The Government has certain rights in this invention.

BACKGROUND OF THE INVENTION

Cell culturing is an essential step in manufacturing many biological products, such as, for example, nucleic acids and antibodies. The process may begin with the addition of a small number of cells (the inoculum) to a vessel containing a liquid media comprising the nutrients essential for metabolism and growth of the cells, and a solid support to which the cells can attach, the solid support immersed in the liquid media. Conditions of temperature, pH, and oxygen and carbon dioxide concentrations are controlled to promote cell growth and division until confluence is reached.

The small scale cultivation and growth of single tissues or tissue grafts on three-dimensional matrices has been described. Use of bioreactors for culturing cells to form a tissue or graft has previously been limited to culturing cells on solid or porous supports suspended in a liquid medium in rigid plastic or glass bioreactors.

Traditional bioreactors are typically designed as stationary reusable tanks or containers. Disposable or single-use bioreactors may utilize plastic sterile bags supported by a non-disposable support structure.

There is a need to develop a flexible wall, disposable bioreactor system for use in ex vivo expansion of cells, tissue, or organs taken from a living body, a system that is designed to provide oxygenation, heat, mixing and pH control as demanded by cells, tissues, grafts, or organs. The ex vivo expanded products could then be transplanted into patients in need thereof. Transplanted tissue can replenish cell population to support regeneration of previously damaged or diseased tissue in the patient. One exemplary use is the growth of vascular cells taken from a living body. Ex vivo expanded vascular cells in the form of a vascular graft could be transplanted into patients in need thereof. Transplanted vascular grafts can support regeneration of previously damaged or diseased vascular vessels in the patient.

Although engineered tissues are increasingly being used in disease therapy in many areas of medicine, for many types of engineered tissues, clinical manufacturing production adheres closely to the original benchtop processes that were used during the early discovery of the technology. Limitations in scale up and automated control of engineered tissue production has led to high costs of goods and potential product variability that may impair clinical outcomes. Hence, there is an urgent need for innovative methods for controllable, scale-able, and affordable tissue production.

Most commercially available vascular grafts are produced from synthetic materials such as expanded polytetrafluoroethylene (PTFE). One yet unsolved problem is that all synthetic grafts suffer from high complication rates when used as arteriovenous (AV) dialysis grafts. These complications can include infection, thrombosis, and neo-intimal hyperplasia leading to graft occlusion. The rates of complications for synthetic AV grafts are so high that the average graft requires multiple interventions during its implantation lifetime, just to maintain patency, that is, the state of being open or unblocked. The high costs of maintaining graft patency, as well as the high morbidity associated with graft infection indicate that there is an urgent need for a better AV graft for dialysis.

Thus, there is an on-going clinical need for a disposable bioreactor system that supports culture, minimizes labor, reduces the risk of breaking sterility, and enables the scale-up production of engineered tissues, organs, and grafts.

SUMMARY OF THE INVENTION

The invention concerns a preferably single-use, single or multiple graft bioreactor that replicates the necessary conditions for growth of cells, including tissues, organs, or grafts. The innovations address: 1) problems in growing the cells in shapes similar to living tissue such as vascular vessels or organs; 2) adaptation to flexible-walled single-use, i.e., disposable bioreactor format; 3) low shear, radial distribution of feed medium to the cells; 4) steady and uniform delivery of pulsatile flow to the tissues growing within the bioreactor; 5) operation as a stand-alone unit that provides the full environmental control required for culture conditions; 6) problems in scaling up tissue growth; and 7) ability to collapse the bioreactor to minimize the inoculum volume.

The invention inter alia includes the following, alone or in combination. In one aspect, the present invention relates to our discovery of a new culture system to achieve ex vivo expansion of cells of animal or human origin in a large scale, stand-alone, disposable bioreactor system, or alternatively, in a disposable culture bag in fluid communication with a disposable bioreactor.

Disposable Culture Bag in Fluid Communication with a Disposable Bioreactor

In one embodiment, the invention relates to a single-use bioreactor system for culturing of a tissue, an organ or a graft, comprising: a disposable cell culture bag having a chamber; a biocompatible scaffold comprising a surface for the attachment of a plurality of cells thereto and growth of thereof, the biocompatible scaffold disposed within the chamber of the disposable cell culture bag; a motion system for cyclically moving the tissue, the organ, or the graft on the surface of the biocompatible scaffold; a disposable bioreactor in fluidic communication through a fluidic pathway with the chamber of the disposable cell culture bag, the disposable bioreactor comprising: a dissolved oxygen sensor; a gas supply system, a pH control system, and a temperature control system, wherein each of the gas supply system, the pH control system, and the temperature control system is configured to control an environmental parameter of a cell culture in the bioreactor system, and is configured to be in operative communication with a fluidic media in the bioreactor system, wherein the fluidic media comprises media for cell growth; and a circulation pump positioned for producing a circulation of the fluidic media through the fluidic pathway between the disposable bioreactor and the chamber of the disposable cell culture bag of the bioreactor system.

A Stand-alone, Single-use, Bioreactor System for Large Scale Culturing

In another embodiment, a stand-alone, single-use, bioreactor system for large scale culturing of a tissue, an organ or a graft, comprises: a disposable bioreactor comprising a chamber having at least one port; a biocompatible scaffold comprising at least one surface for the attachment of a plurality of cells thereto and growth thereof, the biocompatible scaffold disposed within the chamber of the disposable bioreactor; a motion system for cyclically moving the tissue, the organ, or the graft on the at least one surface of the biocompatible scaffold; a re-circulation pump operatively connected to the at least one port of the disposable bioreactor and arranged to circulate a fluidic media inside the chamber, to bring a fresh fluidic media into the chamber, and to remove spent media from the chamber, the fluidic media comprising media for cell growth; a motion system for cyclically moving the tissue, the organ, or the graft on the surface of the biocompatible scaffold; a dissolved oxygen sensor; a gas supply system; a pH control system; and a temperature control system, wherein each of the gas supply system, the pH control system, and the temperature control system is operatively connected to the chamber of the disposable bioreactor, and wherein each of the gas supply system, the pH control system, and the temperature control system is configured to control an environmental parameter of a cell culture in the chamber of the disposable bioreactor.

A Single-use, Single Tissue, Organ, and Graft Bioreactor

In yet another embodiment, a single-use, single tissue, organ, and graft bioreactor for culturing of a single tissue, organ, or graft comprises: a disposable cell culture bag for holding a fluidic media, the disposable cell culture bag having a chamber and a two-way, single port at a surface thereof, the port configured for a function chosen from sampling, inoculation, media influx, media removal, washing, and storage, and combinations of the foregoing; a biocompatible scaffold disposed within the chamber, the scaffold having a passageway therethrough, and comprising an outer surface for the attachment of a plurality of cells and growth thereof; a tubing support structure positioned within the passageway of the scaffold; a device attached to at least one end of the tubing support structure, the device chosen from a compresser, a tensioner, and a twister, and arranged for imparting tension, compression or twisting force on the tubing support structure; a temperature control system configured to control the temperature of a cell culture in the bioreactor; and configured to be in operative communication with the fluidic media in the bioreactor, wherein the fluidic media comprises media for cell growth; and a pump positioned for circulating a fluid through the tubing support structure.

The invention also relates to a method of expanding ex vivo, cells of animal or human origin, comprising: seeding the biocompatible scaffold in any of the bioreactor systems described above or below with a plurality of cells of animal or human origin, while the biocompatible scaffold is bathed in the fluidic media that may be agitated by a magnetically coupled agitator; allowing the cells to attach to the biocompatible scaffold; cyclically moving the attached cells on the surface of the biocompatible scaffold; and circulating the fluidic media for cell growth to continuously bathe the plurality of cells of animal or human origin with the fluidic media under sufficient environmental conditions and for a period of time sufficient to enable the cells to expand ex vivo to form a tissue, graft, or organ.

BRIEF DESCRIPTION OF THE DRAWINGS

The foregoing and other objects, features and advantages of the invention will be apparent from the following more particular description of illustrative embodiments of the invention, as illustrated in the accompanying drawings. In the drawings, reference characters refer to the same or similar parts throughout the different views and embodiments. The drawings are not necessarily to scale; emphasis has instead been placed upon illustrating the principles of the invention. Of the drawings.

DETAILED DESCRIPTION OF THE PREFERRED EMBODIMENTS

Figure 1:
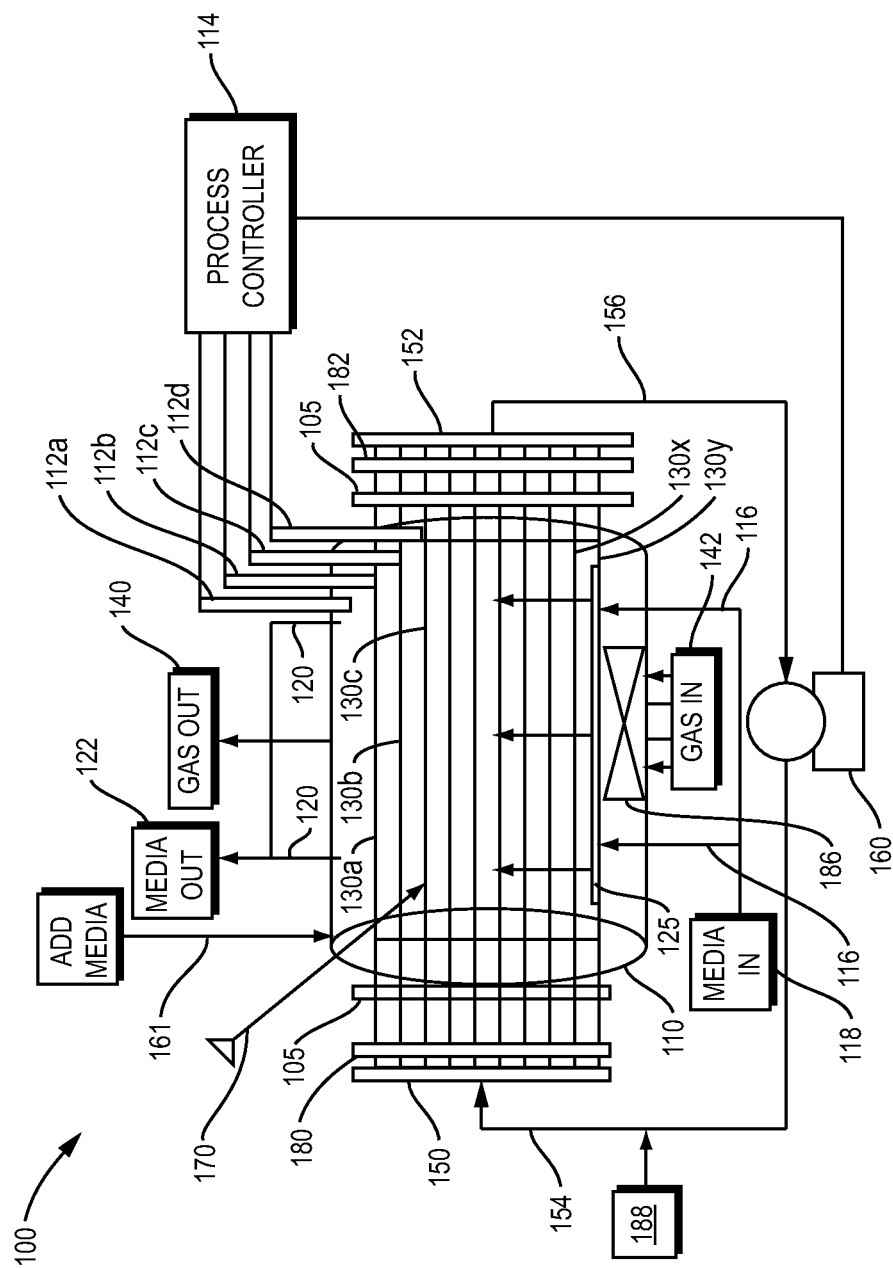
FIG. 1 is schematic diagram of a single-use, single or multiple graft bioreactor according to a first embodiment of the invention that incorporates a support structure perfusion loop and has an in situ agitator.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Throughout the description and claims of this specification, the words "comprise" and "contain" and variations of these words mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Disclosed herein are devices and methods of growing cells, tissues and organs for use in preparation of surgical grafts, including autografts and allografts. An autograft is a graft prepared from the recipient's own tissue, for example from a healthy organ of the recipient. An allograft is a graft of tissue between individuals who are not genetically identical. An allograft may be prepared from tissue obtained from a cadaveric organ or living-related individual, for example.

The invention also relates to a method of expanding cells, for example, mesenchymal cells such as mesenchymal stem cells, which can be activated and mobilised if needed. Mesenchymal stem cells are adult stem cells that can form a variety of cells, including fat cells, cartilage, bone, tendon and ligaments, muscles cells, skin cells, and nerve cells. For example, expanded mesenchymal stem cells could be used to re-generate endocrine tissue, for example, Isles of Langerhans cells for implanting into a patient suffering from diabetes. In another example, although damage to muscles heals very slowly, if mesenchymal stem cells expanded in the disclosed system were activated and implanted in the damaged muscle tissue, then such wounds would very likely heal much faster.

Non-limiting examples of three possible design variations of the disclosed multiple tissue, organ, and graft bioreactor, all achieve the following objectives. Each provides large scale disposable surfaces for growth of multiple tissues, organs, and grafts. Each provides a gas supply system or a gas sparging system, pH control system and temperature control system to meet oxygenation, pH, and temperature demands of multiple tissues, organs, and grafts. Each has the ability to operate in batch, fed batch or perfusion mode.

The following embodiments relate generally to enclosures of support structures that are biocompatible scaffolds for culturing cells, usually forming grafting material such as vascular tissue, vascular grafts, other tissues, and/or organs. A bioreactor vessel system may include a controlled environmental module (CEM) to facilitate growth. It provides a sterile or near sterile environment for seeding inoculation, operation and/or harvest of the finished organ/graft from the bioreactor. See for example, Environmental Containment Systems, US Patent Application Publ. No. US 2008/0139865 A1, by Galliher, et al., and System and Method for Manufacturing, US Patent Application Publ. No. US 2005/0226794 A1 by Hodge, et al., the teachings of both publications being incorporated herein by this reference in their entireties. The CEMs can control temperature, humidity, microbial, and particle count at levels suitable to prevent or minimize the potential for environmental contamination of the bioreactor during seeding, inoculation, operation, or harvesting, or all of these parameters.

In one embodiment of the invention, the biocompatible scaffold has an inner passageway and a surface for attachment and growth of tissues in the media. A motion system is further provided for cyclically moving the tissues on the support structure.

In the preferred embodiments, sensors are provided for monitoring growth conditions for the tissues growing within the bioreactor bag. The sensors include temperature, pH, dissolved oxygen, and carbon dioxide sensors.

Generally, the motion system may produce pulsatile pressure fluctuations within the support structures to provide the necessary growth conditions for vascular grafts, for example. In one embodiment, this motion system comprises a distension and compression system for cyclically distending and compressing the support structure. In other cases, the motion system comprises a pump for cyclically pumping fluid through the passageway in the support structure. Such a system should include a flow divider for distributing the fluid pumped by the pump between multiple support structures. A pressure regulator valve system is also useful for controlling flow and/or pressure between multiple support structures. In another example, a pinch valve system is used that squeezes the support structure to vary a pressure within the support structure.

Preferably, there are one or more ports in the bioreactor vessel bag for introducing inoculate into the bioreactor vessel bag. An inoculation cradle is useful for supporting the flexible, deformable bioreactor vessel bag to facilitate concentration of the support structure in a small volume of inoculate.

Currently, the bioreactor vessel bag is a single use bag, and could comprise the final packaging of the graft prior to use.

When growing vascular grafts, the biocompatible scaffold includes one or more tubes upon which one or more vascular grafts are grown. In other applications, the grafts include one or more organ or tissue grafts grown on the scaffold.

In general, according to another aspect, the invention features a method for culturing cells to form tissues, organs, or grafts. The method comprises providing a bioreactor vessel bag containing a media for cell growth, installing at least one scaffold within the vessel bag. The scaffold may be a solid structure, or may have an inner passageway and a surface for attachment and growth of cells to form tissues. As the tissues grow on the scaffold, the scaffold is cyclically moved to facilitate proper growth.

The bioreactor system can be operated in a batch mode, or in a fed-batch mode in which fresh medium is periodically added into the bioreactor that is agitated by a magnetically coupled agitator. Alternatively, the bioreactor can be perfused continuously by withdrawing medium through porous membranes or disks in the wall of the disposable bioreactor or via the porous tubing or framework while supplying fresh make-up medium to the bioreactor to maintain constant volume.

For either fed-batch or perfusion mode operations, spent medium or fluids can be withdrawn through porous surfaces in the wall of the bioreactor or through the porous tubing framework, while fresh medium is added periodically or continuously to maintain constant volume. Washing solutions or buffer can be applied to the bioreactor in a similar fashion.

Turning now to the figures, FIG. 1 shows schematically a bioreactor system 100 that has been constructed according to the principles of the present invention.

The Scaffold

In the embodiment shown in FIG. 1, the scaffold is arranged horizontally in a disposable bioreactor for forming multiple tissues, organs, and grafts. The biocompatible scaffold could also be arranged in a vertical position or a diagonal position in other embodiments. Yet other configurations of a framework are possible.

The terms "biocompatible scaffold," "biocompatible framework," "biocompatible matrix," "biocompatible substrate", "biocompatible tubing," "support structure," "scaffold," "framework," "matrix," "substrate," or "tubing" (for example, silicone tubing), as used herein, are used synonymously and interchangeably, and refer to a material that is suitable for deposition of a cell population, and which will allow cell growth and expansion. A biocompatible substrate does not cause toxic or injurious effects on a tissue, organ, or graft. In one embodiment, the biocompatible substrate is a polymer with a surface that can be shaped into the desired organ that requires replacing. The substrate can also be shaped into a part of an organ that requires replacing. Cultured populations of cells can be grown on a three-dimensional scaffold which provides pre-determined interstitial distances required for cell-cell interaction. In one embodiment, the biocompatible matrix is biodegradable. Non-limiting examples of biocompatible polymer scaffolds can be polymers formed from materials such as cellulose ether, cellulose, cellulosic ester, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, and copolymers thereof, or physical blends thereof. The polymeric scaffold can be coated with a biocompatible and/or biodegradable material. Those of skill in the art can determine with but limited experimentation, which substrates are suitable for a particular application.

The scaffold can be impregnated with any of a variety of agents, such as, for example, suitable growth factors, stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), insulin-like growth factor (IGF), cytokine growth factor (CGF), stem cell factor (SCF), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), interferon, interleukins, cytokines, integrin, collagen, elastin, fibrillins. fibronectin, laminin, glycosaminoglycans, heparan sulfate, chondrotin sulfate (CS), hyaluronic acid (HA), vitronectin, proteoglycans, transferrin, cytotactin, tenascin, and lymphokines.

The scaffold can be impregnated with a differentiation agent A differentiation agent is any compound which, when added to cells in vitro or introduced into a mammal, result in a change in the phenotype of a cell or tissue, including the expression of one or more markers indicative of a particular stage in the cell's or tissue's life cycle The outside of the scaffold, framework or tubing provides a surface on which cells can attach and grow. The term "attach" or "attaches" as used herein, refers to cells adhered directly to the scaffold or to cells that are themselves attached to other cells. The framework or tubing may be permeable to gases or liquids, depending upon its chemical make-up or porosity. If porous to liquids, fresh or spent medium can be exchanged through the walls of the tubing. Alternatively, a porous or a non-porous tubing can be used to remove wastes or to transport fresh medium to the tissues, organs, and grafts growing on the framework. Inoculation of the bioreactor could also be achieved through a porous tubing or framework. If the framework or tubing is permeable to gases, oxygen supply and $CO_2$ removal could be accomplished through the framework or tubing.

A non-limiting example of a porous material that would be suitable for use in a scaffold according to an embodiment of the invention is a porous matrix prepared from collagen and chondroitin sulfate with some cross-linking with glutaraldehyde. Another example is a bioabsorbable material such as a high-molecular-weight polymer of polylactide or polylactic acid (PLA).

The grafting material is grown on one or more scaffolds or support structures 130 contained within vessel 110. In one embodiment, vessel 110 contains multiple support structures 130a, 130b, 130c, . . . 130x, 130y.

In one embodiment of the invention, scaffolds 130 have inner passageways therethough. In one implementation, the scaffolds are hollow tubes, such as silicone tubes, that form a tubular culture scaffold that is bathed in the growth media or fluidic media contained or circulating through vessel bag 110.

The outside of support structure or tubing 130 provides a surface for an appropriate scaffold on which cells attach and grow. See for example, U.S. Pat. No. 6,537,567 and U.S. Pat. No. 6,962,814, the teachings of which are incorporated herein by reference in their entireties. In one embodiment, the biocompatible scaffold comprises a hollow tubing having a mesh material or a porous material, such as polyglycolic acid (PGA) at an external surface of the hollow tubing, forming a scaffold, jacket or sock-like covering over tubing 130 upon which cells can attach and grow.

In the case of growing organs or other tissues, other support structures with inner passageways are used such as hollow mandrels, cylinders, spheres, and cubes or any shape that will promote organ growth and has an inner passageway.

The Tensioning System

The port(s) at the junction of the scaffold, tubing, or support structure 130, and the bioreactor bag 110 are specially designed and reinforced to allow the application of tension to the support structure 130 by activating tubing tensioners 105, such that the organ/graft being enlarged on the support structure 130 will be true and straight. The flexible wall of the bioreactor bag 110 eases the application of tension on the support structure 130 without risk of breaching connections of the tubing to the bioreactor wall, as is the case with rigid vascular graft bioreactors.

Figure 2:
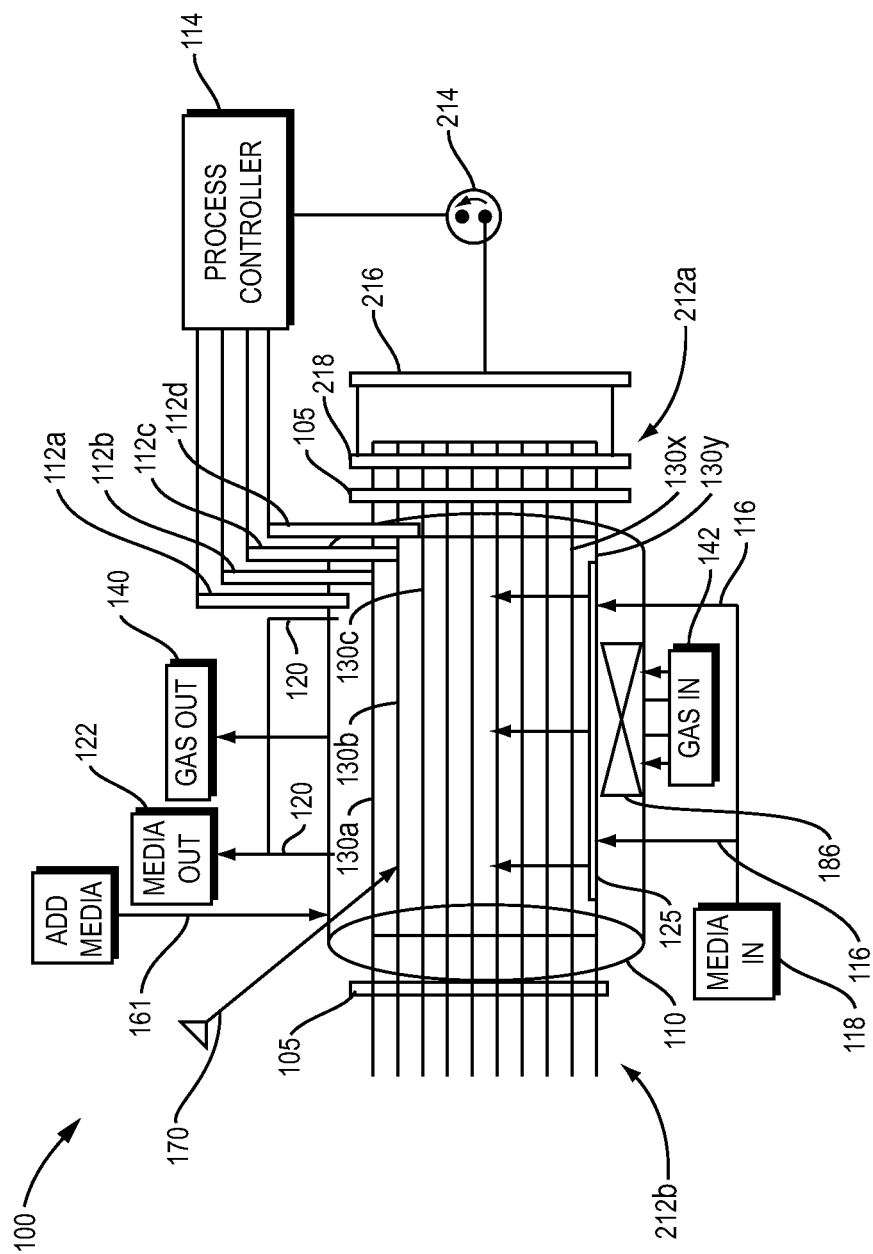
FIG. 2 is schematic diagram of a single-use, single or multiple graft bioreactor according to a second embodiment of the invention without a support structure perfusion loop but including a mechanical distension and compression system for cyclically distending and compressing the support structure using a mechanical system, and in situ agitator.

FIG. 2 schematically depicts a further embodiment of the invention, wherein a ridged frame 216, 218 is provided in vessel 110, which serves to hold the scaffold 130 at a defined position within the bioreactor vessel 110, and to prevent kinking or bending of the tubing, for example. Tubing tensioners 105 are also shown in FIG. 2. In some embodiments for other applications, the frame 216, 218 might obviate the need for a tensioning system. In other embodiments, other frames 216, 218 are provided inside bioreactor vessel 110 with different shapes for other tissues, such as planar or spherical tissues.

Control of pressure within the tubing via a pump 160 that controls flow rate through the tubing: Turning back to FIG. 1, control of pressure within the tubing via a pump 160 provides uniform distention and pulsing of the tubing. This is accomplished with a flow distributor or manifold 150, 152 on the input line 154, and pinch valves 182 on the output line 156, that are designed to eliminate differences in flow rates and pressures across the different grafts within the bioreactor imposed by hydrodynamic pressures and forces.

Figure 6:
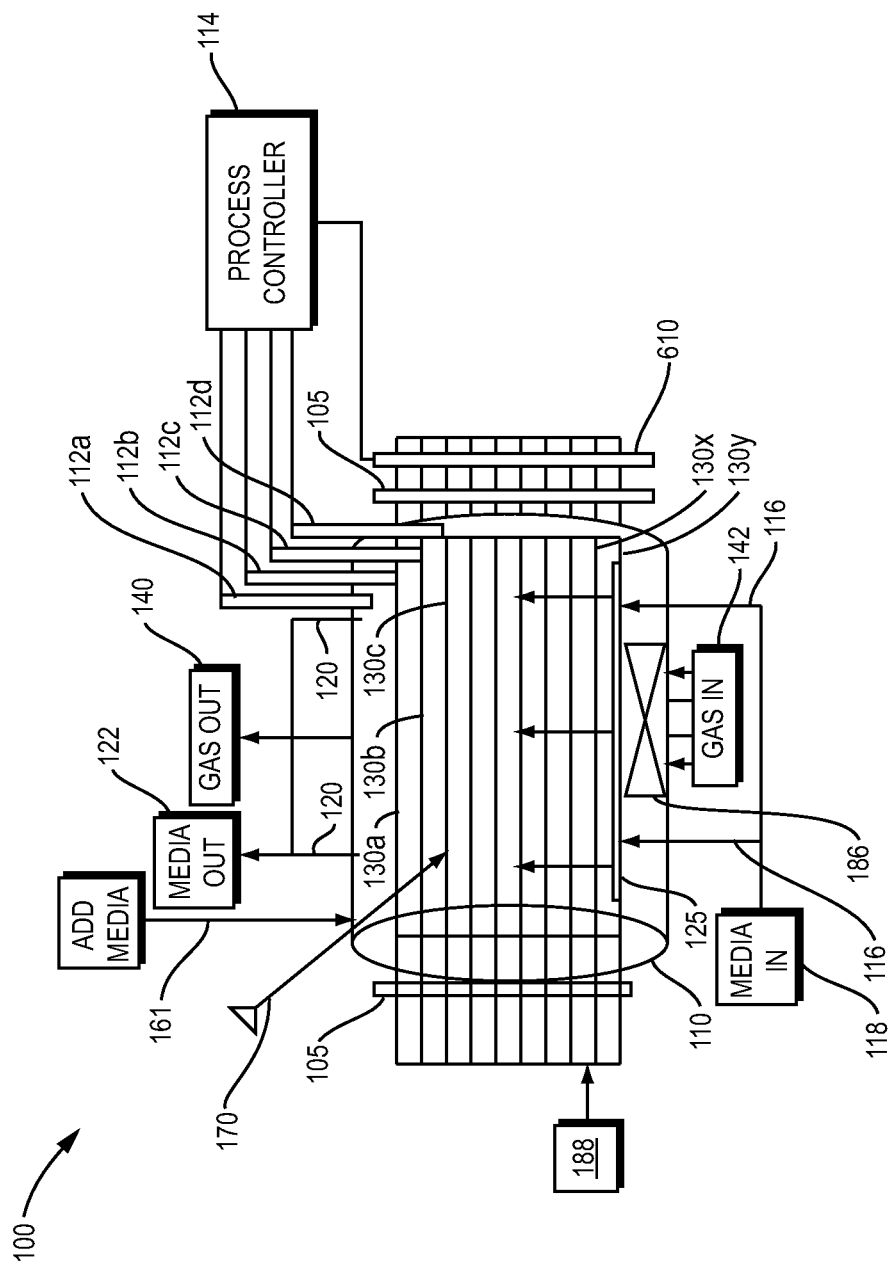
FIG. 6 is schematic diagram of a single-use, single or multiple graft bioreactor that is agitated by a magnetically coupled agitator according to another embodiment of the invention without a support structure perfusion loop but including a pinch valve array for compressing the support structure using a mechanical system.

Control of pressure in the tubing via tubing compression: As shown in FIG. 1, and FIG. 6 and described below, in another embodiment, control of pressure in the tubing can be accomplished without a pump by applying compression to the sealed end of the tubing via pinch valves 182 in FIGS. 1 and 610 in FIG. 6. This compression can increase and decrease pressure in a pulsating fashion to simulate in-vivo systolic and diastolic pressure fluctuations, thereby cyclically pressurizing the flexible tubing within the graft, and achieving the same type of pressurization and distension that is achieved by pumping fluid through the tubing. A process controller 114 is used to control the cyclic compression of the tubing.

Control of pressure in the tubing via tubing distention: In another embodiment described below, control of pressure can be accomplished without a pump by applying distention to the sealed end of the tubing.

The Collapsible Bag

The bioreactor 100 comprises a vessel 110 for containing the biologically active material such as matrices of cultured cells forming grafting material such as vascular tissue, vascular grafts, other tissues, and/or organs. In the preferred embodiment, the vessel 110 is a flexible and collapsible bag.

In one embodiment of the invention, vessel 110 is housed in an incubator environment such as in a jacketed, heated/cooled shroud or tank (not shown) that protects and provides mechanical support for vessel 110.

Better aseptic control is provided by using the flexible and collapsible bag 110. Use of a fully gamma-irradiated plastic or polymeric bioreactor bag that does not require risky open, manual manipulation in biosafety cabinets is preferred. Improved ease of use is provided by a polymeric, single use or disposable system that is not susceptible to breakage (as is a glass bioreactor) and which does not require cleaning, because it is single use system. The flexible wall of the bioreactor bag enables collapsing of the bag, such that the scaffold is lowered to the bottom of the bag, enabling the delivery of concentrated inoculum cells directly onto the scaffold. The finished grafts can be washed and stored, preferably in the same bioreactor bag in which they were grown. The bag can then be shipped to the point of use without exposing the grafts to the environment.

Sensors

A series of sensors 112 are used for monitoring the environment within and potentially adjacent to the vessel 110. In one example, the sensors 112 are in-situ single use sensors, such as a pH sensor 112A for monitoring pH of the fluid within the vessel 110, a temperature sensor 112B for monitoring the temperature of the fluid contained within the vessel 110, a dissolved oxygen sensor 112C for monitoring oxygen within the fluid, and a carbon dioxide sensor 112D for measuring carbon dioxide concentrations. In other examples, glucose and lactate and/or ammonia sensors are further provided for measuring glucose and/or lactate and ammonia concentrations for the fluid.

In one example, sensors 112 communicate with the interior of vessel 110 via sterile connecting ports. In other examples, the sensors 112 are provided already-assembled into the bioreactor vessel bag prior to gamma irradiation and not re-used, but discarded with vessel bag 110.

In other implementations, different or additional sensors are used to monitor the material within vessel 110 and otherwise assess progress of the biological processes taking place within vessel 110.

The sensors 112 are monitored by a process controller 114 that modulates growth parameters within vessel 110 through feedback control. Process controller 114 generally monitors the conditions within vessel 110 and controls bioreactor system 100 in order to optimize the growth of the cells, tissues, grafts, and/or organs that are being cultured and expanded within vessel 110.

Fluid Supply and Fluidic Media Distribution

Growth media, or fluidic media, is added to the fluid and other material contained within vessel 110 via media feed ports 116 from a growth media supply tank 118. In one embodiment, the media feed ports 116 terminate in a distribution system 125 that is contained within vessel 110. In one embodiment, distribution system 125 is a radial flow, in situ fluidic medium distribution system, the system ensuring that the replenishing growth media solutions are evenly distributed in a low shear, radial fashion across the scaffolds within the vessel. As used herein, the term "radial flow" means that the flow is approximately perpendicular to the axis of a scaffold 130. Further, an in-situ agitator 186 is further provided in order to distribute and mix the media in vessel 110, in a preferred embodiment.

The growth media and any waste material exit vessel 110 via media exhaust ports 120 and carry the media and other material to a reservoir 122 or back to the growth media supply tank 118.

The feed and exhaust ports 116, 120 usually also convey fluids, such as, for example, inoculum, feeds, inducers, nutrients, and pH control fluids, and later, washing and de-cellularization fluids. In some examples, the ports 116, 120 are single or multiple two-way port(s) that allow inflow and/or outflow of the fluids.

In the embodiment of FIG. 1, the ends of the tubular support structures 130a, 130b, 130c, . . . 130x, 130y terminate in a first manifold 150 and a second manifold 152. The manifolds 150, 152 are tubing flow distributors, and are connected in a recirculating tubing perfusion loop through input line 154 and output line 156 that connect to a pump 160.

In the case of growing vascular grafts type tissues, the attachment and expansion of cells on the scaffold occurs while liquid is pumped through the passageways in the support structure 130 such as inside the tubing 130a, 130b, 130c, . . . 130x, 130y. The liquid provides the pulsing required to create cyclic motion in the cellular matrices, such as vascular grafts, that allows for proper growth. This pulsing is achieve by the operation of the pulsation pump 160, which is controlled by the process controller 114, applying a pulsing action to the support structures 130 by increasing and decreasing the pressure of the liquid pumped inside the silicone tubing. This is critical to the proper growth of the vascular cells on the outside surface of the tubing 130, and may also be important for the growth of non-vascular tissue and organs. Additional fluids can also be supplied to or from the support structures 130 via feeding into the re-circulating tubing using ports in the pump 160 or the input or output lines 154, 156. In other case, if permeable, the fluids can perfuse the tubing directly.

Control and equalization of pressure within the support structure 130 and between the tubing 130a, 130b, 130c, . . . 130x, 130y is improved by further including a flow divider 180 on the inlet side and an array of pinch valves 182 on the outlet side. The flow divider 180 and pinch valves array 182 function to eliminate or minimize differences in flow rates and pressures across the different tubes 130a-130y of the support structure 130. In this way, each of the grafts within the bioreactor vessel 110 are exposed to the same hydrodynamic pressures and forces.

pH control and carbon dioxide control are achieved in some embodiments of the invention through gassing of the vent space 140 of bioreactor bag 110 or via gassing through port 188 of the re-circulating liquid passing through support structures (tubing) 130, or both. Addition of acid or alkali or buffers through the two-way addition port on the bioreactor vessel 160 or into the permeable recirculation tubing at port 188, or both can be utilized to control pH.

Dissolved oxygen control is achieved via any or all of the following: gassing of the vent space of the bioreactor bag via port 140; gassing of the recirculating liquid passing through the support structures 130, at port 188; or sparging the gas into the bioreactor near or under the agitator.

Glucose or growth media is directly supplemented through vessel ports 116 into vessel 110 in some embodiments; and control of lactate and ammonia is effected by replenishment of culture medium inside the vessel. In other cases, these nutrients are fed or perfused through the cells or tissue growing on the scaffold via the porous tubing components of the scaffold by addition through port 188.

In some embodiments, one or more injection ports 170, such a septum injection port, are provided in vessel 110. These are used for inoculating the starting cells onto the surface of the support structure 130. The flexible nature of the single use bioreactor bag 110 improves the ease with which inoculum cells are injected via the septum port 170 directly onto the support structure 130. Contact of the cells with the support structure 130 is enhanced by partially evacuating the bag 110 to remove air via a sterile vent filter. This concentrates the inoculum fluid directly onto the support structure until cell attachment occurs. After cell attachment, the vessel 110 is refilled and inflated to its operational size for the growth of the cells on the support structures 130.

Alternative Design for Motion System Without Pumping Fluid Through the Tubing

FIG. 2 shows an alternative design comprising a motion system for the tissues or grafts on a scaffold, but without requiring re-circulating the fluidic media through tubing perfusion loop 154, 156 and pump 160 depicted in FIG. 1, and without pumping of any fluid through the passageway in the support structure. Similar reference numerals have been used to denote similar components and associated functions to the embodiment shown in FIG. 1.

In this design, the support structure 130 is mounted inside the bioreactor vessel bag 110 with portions 212*a*, 212*b* of the support structure 130 protruding outside the bag 110.

In the illustrated embodiment support structure portion 212*a* is mechanically attached to a reciprocating motor 214 via frame members 216, 218. A clamp 218 is fastened to the end of the tubing 130, and frame 216 connects to the clamp such that frame 216 is moved back and forth by the distensioner motor 214. In this example, the rotation motion of the motor 214 is converted into a reciprocating motion that results in the cyclic compression and distention of the support structure 130 within the vessel 110. The motion cyclically moves the cells or tissues that are being grown or expanded on the support structure 130 under control of the process controller 114. In this way, movement is applied to the tissues, organs, or grafts growing on the support structure 130 to manipulate the grafts within the bioreactor vessel 110. Compression and pressure increases and decreases in a pulsating fashion simulate in-vivo systolic and diastolic pressure fluctuations, thereby cyclically pressurizing the flexible tubing within the graft, and achieving a similar type of pressurization and distension that is achieved by pumping fluid through the tubing.

In other embodiments, the motor 214 is a linear motor or other machine that applies motion to the support structure 130 such as a twisting motion to manipulate the organ graft within the bioreactor.

Cell Culture Seeding Methods

Figure 3A:
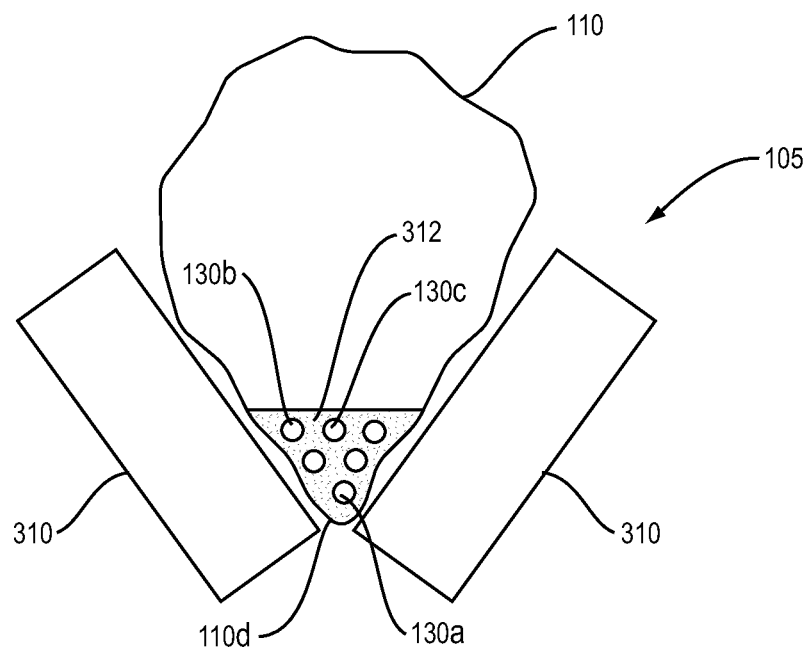
FIG. 3A is a partial sectional view of a bioreactor in a concentrator cradle, according to another embodiment of the invention.

FIG. 3A is a cross-section in the lateral direction showing a cradle mechanism 115 for supporting vessel bag 110 during inoculation of the support structure 130. The bioreactor bag 110 is placed on a cradle 310. In other implementations, the cradle 310 and bag 110 are moved vertically into contact with each other. The cradle has a "V" shaped cross-section that forms a depression 110*d* along the center line of vessel 110.

Figure 3B:
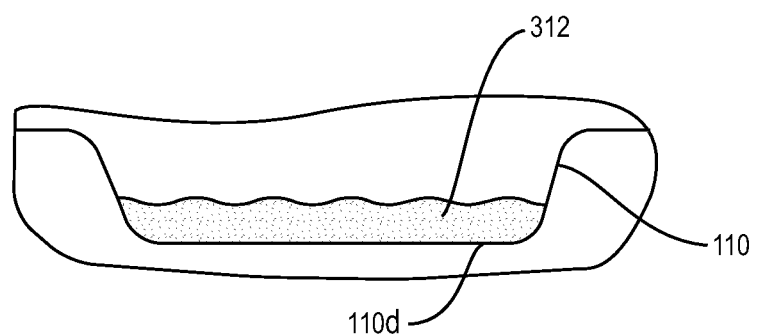
FIG. 3B shows a longitudinal profile of the flexible, deformable bioreactor vessel with a depression for facilitating inoculate concentration.

FIG. 3B shows the profile of vessel 110 in the longitudinal direction. Vessel 110 includes an expanded region that further facilitates the concentration of a relatively small volume of inoculum 312 in a small region of vessel 110.

In operation, when the inoculum fluid is injected such as through septum port 170 (See FIGS. 1, 2, and 6), the support structure, such as tubing 130A, 130B, 130C . . . , is manually lowered into the depression 110D, which results in the concentration of the inoculum solution 312 around the support structure 130. Following cell attachment to support structure 130, bioreactor vessel 110 is mounted in its permanent chamber or external support, filled to working volume, and inflated with air for growth of cells.

In a further embodiment, the inoculum is added directly to the inflated bioreactor vessel 110 after which the cells are entrapped on the scaffold surface upon agitation of the culture within the bioreactor vessel 110.

Harvest of Tissue Organ or Graft

After vascular or organ graft growth, the bioreactor 110 is drained and then filled with a decellularizing solution which removes all cells from the graft to render it immunologically neutral for use as a surgical vascular graft implant.

Harvesting the final organ or graft is facilitated by a "zip lock" type opening in bioreactor bag 110, the opening positioned in a convenient location for removal of the fully grown grafts. This feature avoids the need to cut open the bioreactor surface with a knife or scissors which could contaminate the organ or graft. In another embodiment, bioreactor 110 is wrapped in an outer liner, which preserves sterility of the bioreactor and its contents until it is opened by the surgeon.

Packaging of the finished graft includes a decellurization liquid wash, followed by an inert gas such as nitrogen or argon to enhance shelf life and prevent spoilage.

Figure 4:
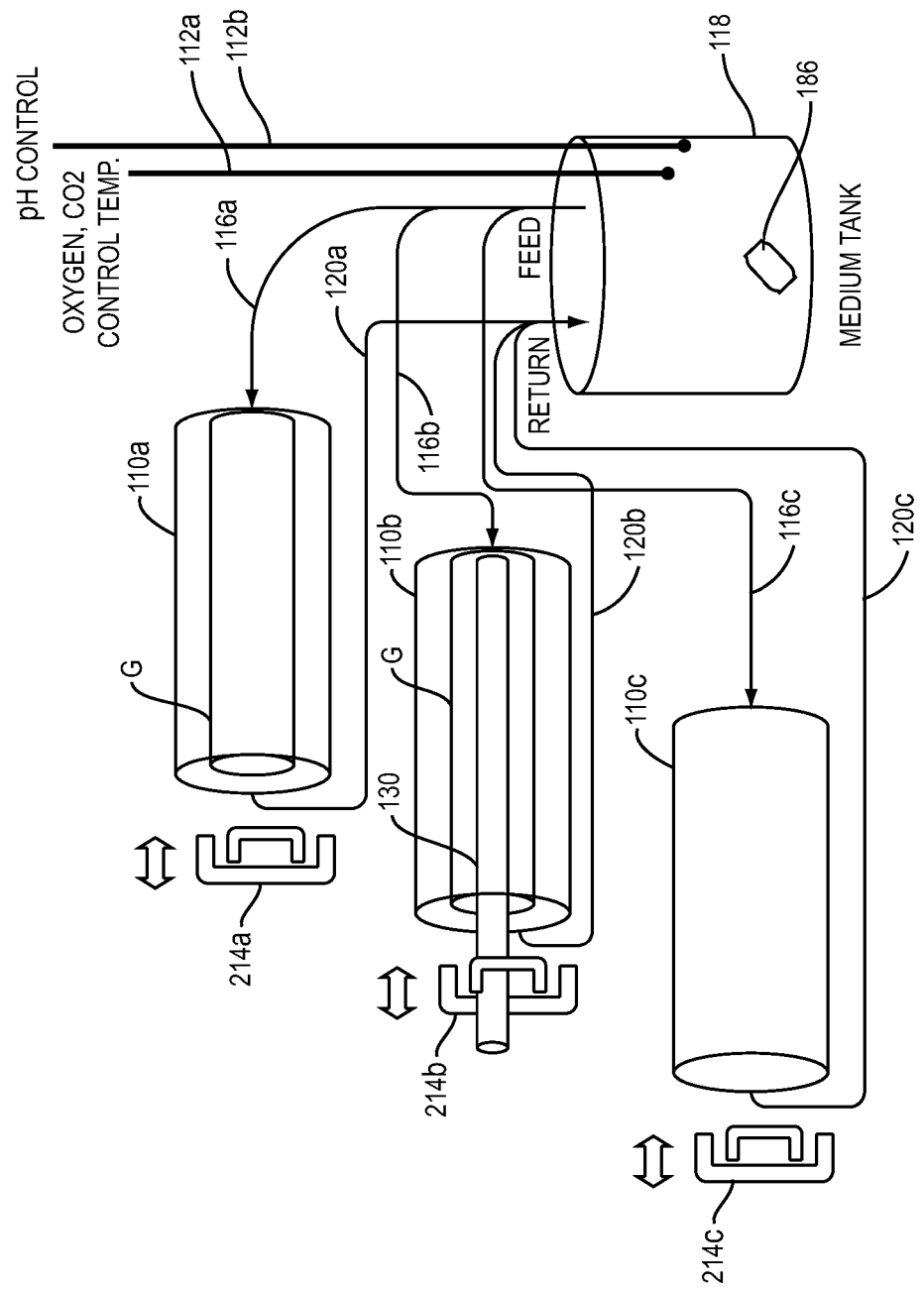
FIG. 4 is a schematic diagram of a plurality of single-use bioreactor vessels or cell culture bags containing individual vascular grafts being fed growth media from a common tank or bioreactor that is agitated by a magnetically coupled agitator according to a third embodiment.

Disposable Bioreactor in Fluidic Communication with Chamber of a Disposable Cell Culture Bag/Bioreactor FIG. 4 shows another embodiment of bioreactor 100 which is then constructed according to the principles of the present invention.

Generally, this embodiment includes separate cell culture bags or bioreactor vessels 110A, 110B, 110C for each of the scaffolds, for example tissue, vascular graft, or organ. Each of the cell culture bags or bioreactor vessels 110 is supplied with the growth media via a common growth media supply tank 118. The media supply tank 118 can be a disposable bioreactor which includes sensors, control systems for oxygen, temperature, and pH control, and an agitation or stirring mechanism 186.

In the illustrated example, the bioreactor vessel or cell culture bag 110*a* includes a graft G. Similarly, bioreactor vessel 110*b* includes a graft G around a support structure 130. Finally, a third bioreactor 110 C is further provided.

Each of the cell culture bags or separate bioreactors 110 includes a corresponding media feed ports 116. For example, bioreactor vessel 110*b* is supplied with growth media via a dedicated media feed 116*b*. In one example, as illustrated, the media is preferably fed from bioreactor or medium tank 118 to the support structures or tubes on which the graphs G are being grown or enlarged.

Media is returned from each of the vessels 110 via immediate exhaust ports 120. For example, vessel 110*b* contains growth media in the reservoir surrounding the graft G, which is carried to the growth media tank or bioreactor 118 via exhaust port 120*b*.

The growth media tank 118 preferably includes a series of sensors for monitoring the growth media contained in the tank 118. In the illustrated example, an oxygen, carbon dioxide and control temperature sensor 112*a* is provided along with a pH sensor 112*b*.

Preferably, a motor 214 is associated with each of the graphs G in each of the vessels 110. In one implementation, the motor 214 can be operated to cyclically extend and compress the support structure 130 associated with each of the grafts G. For example, motor 214b cyclically extends and retracts the support structure 130 within the bioreactor vessel 110b.

In operation, each of the grafts G grows separately from the others in each of the vessels 110a, 110b, 110c, respectively. This allows the grafts G to be separately harvested and transported in their separate cell culture bags or bioreactor vessels 110 for implantation. This embodiment of the invention reduces the risks associated with removal and repackaging of the grafts. The grafts need never be touched until they are removed by the surgeon either by cutting the bioreactor vessel 110 or accessing the graft via a "zip lock" type closure mechanism.

Figure 5:
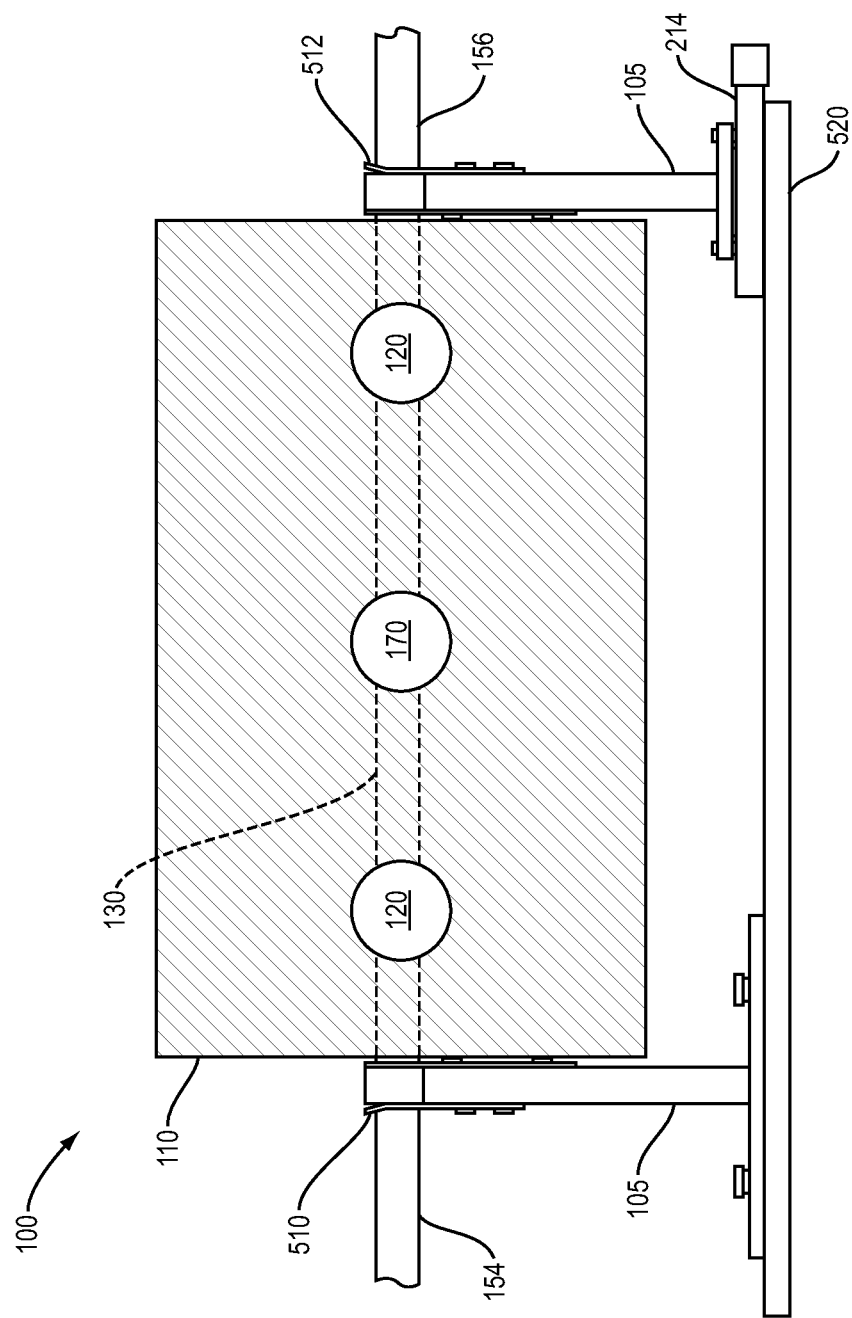
FIG. 5 is a side plan scale view of a cell culture bag or bioreactor for growing a single graft on a support tubing with pulsatile flow therethrough according to another embodiment.

FIG. 5 is a side elevational view of another embodiment of the bioreactor system 100. In this embodiment, a disposable bioreactor (not shown) is in fluidic communication with a chamber of a disposable cell culture bag 110. An inoculation port 170 is shown on the side of bag 110 positioned between two extralumen media outlet ports 120. In this example, an extralumen media inlet port (not shown) is located on the opposite side (not shown) of the bag. A single scaffold, support structure, or tubing 130 is held mechanically by a support frame 105. Collets 510, 512 are provided in support 105 for holding the tubing 130 and connecting it to tensioning device 520 with linear slide 214.

The support 105 shown at the right sits on a linear slide 214 that connects the support to the underlying frame of tensioning device 520. This linear slide 214 can be mechanically moved to impart tension to the tubing 130.

In one embodiment, the linear slide can be connected to a motor means that cyclically moves to the left and right to cyclically distend and compress the support structure 130 contained in the vessel 110 to thereby provide pulsatile movement to the support structure 130 and the tissue that is being grown or expanded on the support structure.

The channel or lumen in tubing 130 is fluidly connected to an intralumen pulsatile flow inlet 154 at the left, and to an intralumen pulsatile flow outlet 156 at the right. The fluid used for the intralumen pulsatile flow could be any suitable liquid, or in a particular embodiment could be fluidic media. A pulsatile pump (not shown) can be used to pump a liquid through the lumen in tubing 130. A circulation pump (not shown) can be used to produce a circulation of the fluidic media through a fluidic pathway between the disposable bioreactor and the interior or chamber of the disposable cell culture or bioreactor bag 110.

FIG. 6 shows still another embodiment. Similar reference numerals have been used to denote similar components and associated functions to the embodiments shown in and described with respect to FIGS. 1 and 2.

In this embodiment, the motion system for the cellular matrices on the support structures is provided by pneumatic pinch valve array 610. The valve array is located on one end of the support structure and specifically each of the tubes 130a, 130b, 130c, . . . 130x, 130y. The tubes are sealed at both ends. The valve array 610 intermittently flattens each of the tubes 130a, 130b, 130c, . . . 130x, 130y under control of the process controller 114. This increases its pressure to thereby provide motion to the tissues growing on the tubes 130.

Some Features of Bioreactors According to Embodiments of the Invention

A single use bioreactor system for culturing of a tissue, an organ or a graft, may include, for example: a disposable cell culture bag having a chamber; a biocompatible scaffold having a surface for the attachment of a plurality of cells thereto and growth of thereof, the scaffold disposed within the chamber of the cell culture bag; a motion system for cyclically moving the tissue, the organ, or the graft on the surface of the biocompatible scaffold; a disposable bioreactor in fluidic communication through a fluidic pathway with the chamber of the cell culture bag, the disposable bioreactor comprising: a dissolved oxygen sensor; a gas supply system which could be a porous frit or membrane used for gas sparging; control systems for controlling pH, temperature, wherein each of the gas supply system, the pH and the temperature control systems configured to control an environmental parameter of a cell culture in the bioreactor system, and is in operative communication with a fluidic media in the bioreactor system, wherein the fluidic media comprises media for cell growth; and a circulation pump positioned for producing a circulation of the fluidic media through the fluidic pathway between the disposable bioreactor and the chamber of the disposable cell culture bag. The disposable cell culture bag may also be described as a bioreactor, e.g., bioreactor 110, as shown in FIGS. 4 and 5.

In this bioreactor system, the motion system produces a plurality of pulsatile pressure fluctuations within the scaffold. The motion system may include a distension and compression system for cyclically distending and compressing the scaffold.

The bioreactor system may include at least one port for introducing an inoculate into the cell culture bag.

The fluidic communication of the disposable bioreactor with the chamber of the disposable cell culture bag may be continuous during use, wherein the circulation pump circulates the fluidic media through the fluidic pathway in a continuous, perfusion mode; or the fluidic communication with the chamber of the cell culture bag may be periodic during use, such as in a batch mode or a fed batch mode.

The scaffold of the disposable bioreactor may comprise a hollow tubing having an inner passageway, and the motion system may include a pulsation pump associated with the disposable cell culture bag, the pulsation pump configured for cyclically pumping a fluid through the inner passageway, so as to produce a plurality of pulsatile pressure fluctuations within the hollow tubing. In some embodiments, the circulation pump that circulates fluidic media through the fluidic pathway may be a pulsation type pump, and also cyclically pump the fluidic media through the inner passageway.

The single-use bioreactor system may comprise a mesh material or a porous material, e.g., PGA, at an external surface of the hollow tubing. The hollow tubing may be sufficiently porous to allow inoculation of the disposable cell culture bag through the hollow tubing. The tubing or scaffold may be arranged horizontally or vertically within the chamber of the disposable cell culture bag.

It should be noted that a disposable bioreactor according to an embodiment of the invention may be a stand alone bioreactor or it may be a bioreactor or cell culture bag having a scaffold for the growth of tissues thereon and wherein the chamber housing the scaffold is fluidly connected to another bioreactor which has sensors and environmental controls. In any of the embodiments of the disposable bioreactor described herein, there may be more than one pump. A pump described herein may be a circulation pump or a re-circulation pump, or a pulsatile pump. However, the type of pump described in a particular embodiment should not be limited to any particular type, as any type of pump is within the scope of the invention. Further, any of the disposable bioreactors according to an embodiment may include a magnetically coupled agitator.

It should also be noted that, for a non-vascular graft or tissue the support structure does not need to be hollow. In one embodiment, the support structure, and/or the center of the support structure may be made of a bioabsorbable or a biodegradable material.

Methods of Expanding Cells or Tissue

The invention also relates to a method of expanding ex vivo, cells of animal or human origin, comprising: seeding the biocompatible scaffold in any of the bioreactor system s described herein with a plurality of cells of animal or human origin, while the biocompatible scaffold is bathed in the fluidic media; allowing the cells to attach to the biocompatible scaffold; cyclically moving the attached cells on the surface of the biocompatible scaffold; and circulating the fluidic media for cell growth to continuously bathe the plurality of cells of animal or human origin with the fluidic media under sufficient environmental conditions and for a period of time sufficient to enable the cells to expand ex vivo to form a tissue, graft, or organ.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention.

EXEMPLIFICATION

Example

Culture of Human Single or Multiple Vascular Graft (SMVG) in a Flexible, Disposable Bioreactor System According to an Embodiment of the Invention Human vascular smooth muscle cells (SMC) were isolated by explant culture from segments of cadaveric human aorta. Human SMC at passage 2 were used for the culture of SMVG in the flexible bioreactor.

Tubular polymer scaffolds for SMC culture that were 6 mm in diameter were made from non-woven mesh of polyglycolic acid fibers, and were attached at either end to segments of polyethylene teraphthalate (PET, or Dacron) tubing. Polymer scaffolds with Dacron end-segments were threaded over distensible silicone tubing, and mounted on connectors that allow for tensioning of the scaffold tubing.

Individual disposable bioreactors or cell culture bags (see FIGS. 4 and 5) were constructed from sheets of high-density polyethylene and fitted with connecting ports that allow for cell inoculation. The disposable bioreactors were fashioned to contain the polymer scaffolding and silicone tubing that was connected to tensioning connectors, which were incorporated into the flexible wall of the bioreactor. In this way, tensioning connectors extended into the bioreactor to provide suspension of the polymer scaffold and silicone tubing, and the connectors also extended outside of the bioreactor to be held by the tensioning device to provide tension to the scaffolding inside of the bioreactor.

The flexible bioreactors were also fashioned to contain input and output ports for media perfusion. Occlusive connectors were fitted to all tubing and ports extending outside of the bioreactor, and the bioreactor was sterilized by gamma irradiation.

After sterilization, the human SMC were cultured in standard tissue culture flasks in Dulbecco's Modified Eagles Medium (DMEM) containing 20% human serum, amino acids, and ascorbic acid supplementation. SMC were released from flasks by trypsinization, and were concentrated to 5 million cells per mL of culture medium. Ten mL of medium was inoculated through the inoculation ports into the sterile flexible bioreactor bag.

The polymer scaffold was manually displaced down into a trough in the flexible bioreactor, which allowed for the scaffolding to be brought into direct contact with the culture medium containing the SMC suspension (see FIGS. 3a and 3b.). In this way, medium was inoculated directly onto the polymer scaffold with high efficiency in only 20-30 minutes.

After this inoculation step, the bioreactor bag was filled with culture medium and connected to the perfusion system for continuing culture medium feeding. Results from this system show that the polymer mesh can be efficiently inoculated with cells, and the bioreactor system remains sterile for cell culture for the entirety of the culture period.

EQUIVALENTS

While this invention has been particularly shown and described with references to preferred embodiments thereof, it will be understood by those skilled in the art that various changes in form and details may be made therein, and that the principles and features of this invention may be employed in various and numerous embodiments without departing from the scope of the invention encompassed by the appended claims.

What is claimed is:

1. A single-use bioreactor system for culturing of a tissue, an organ or a graft, comprising:
   a controlled environmental module configured to facilitate cell growth and to provide a sterile environment for seeding, operation, and/or harvesting of a finished organ or graft from the single-use bioreactor system;
   a disposable, flexible cell culture bag having a chamber and one or more injection ports;
   a biocompatible scaffold comprising a surface for the attachment of a plurality of cells thereto and growth of thereof, the biocompatible scaffold disposed within the chamber of the disposable cell culture bag;
   a motion system for cyclically moving the tissue, the organ, or the graft on the surface of the biocompatible scaffold;
   a disposable bioreactor in fluidic communication through a fluidic pathway with the chamber of the disposable cell culture bag, the disposable bioreactor comprising:
      a dissolved oxygen sensor;
      a gas supply system,
      a pH control system, and
      a temperature control system, wherein each of the gas supply system, the pH control system, and the temperature control system is in operative communication with a process controller that is configured to control an environmental parameter of a cell culture in the bioreactor system to modulate one or more growth parameters within the bioreactor system through feedback control, and is configured to be in operative communication with a fluidic media in the bioreactor system, wherein the fluidic media comprises media for cell growth; and
   a circulation pump positioned for producing a circulation of the fluidic media through the fluidic pathway between the disposable bioreactor and the chamber of the disposable cell culture bag of the bioreactor system,
   wherein the controlled environmental module is further configured to provide for inoculating starting cells through the one or more injection ports and onto the surface of the scaffold while the culture bag is disposed therein.

2. The single-use bioreactor system of claim 1, wherein the gas supply system comprises a gas sparger.

3. The single-use bioreactor system of claim 1, wherein the motion system produces a plurality of pulsatile pressure fluctuations within the biocompatible scaffold.

4. The single-use bioreactor system of claim 1, wherein the motion system comprises a distension and compression system for cyclically distending and compressing the biocompatible scaffold.

5. The single-use bioreactor system of claim 1, wherein said one or more ports in the disposable cell culture bag introduce an inoculate into the disposable cell culture bag.

6. The single-use bioreactor system of claim 1, further comprising an inoculation cradle that supports the disposable cell culture bag, the inoculation cradle being so shaped that an inoculate within the disposable cell culture bag increases in concentration at the biocompatible scaffold when the disposable cell culture bag is collapsed or the biocompatible scaffold is lowered into the inoculate, the increased concentration of the inoculate facilitating attachment of the plurality of cells to the biocompatible scaffold.

7. The single-use bioreactor system of claim 1, wherein the fluidic communication of the disposable bioreactor with the chamber of the disposable cell culture bag is configured to be continuous during use, and wherein the circulation pump is positioned for circulating the fluidic media through the fluidic pathway in a continuous, perfusion mode.

8. The single-use bioreactor system of claim 1, wherein the fluidic communication of the disposable bioreactor with the chamber of the cell culture bag is configured to be periodic during use, and the system is configured for a batch mode or a fed batch mode.

9. The single-use bioreactor system of claim 1, wherein the biocompatible scaffold comprises a hollow tubing having an inner passageway therethrough, and the motion system comprises a pulsation pump associated with the disposable cell culture bag, the pulsation pump configured for cyclically pumping a fluid through the inner passageway, so as to produce a plurality of pulsatile pressure fluctuations within the hollow tubing.

10. The single-use bioreactor system of claim 9, further comprising a mesh material or a porous material at an external surface of the hollow tubing.

11. The single-use bioreactor system of claim 9, wherein the hollow tubing is sufficiently porous to allow inoculation of the disposable cell culture bag through the hollow tubing.

12. The single-use bioreactor system of claim 1, wherein the biocompatible scaffold is arranged horizontally or vertically within the chamber of the disposable cell culture bag.

13. The stand-alone, single-use, bioreactor system of claim 1, wherein the wherein the biocompatible scaffold includes at least one tissue graft or organ graft.

14. The single-use bioreactor system of claim 1, further comprising a pinch valve system that squeezes a portion of the tubing to vary a pressure within the tubing and thereby cyclically pressurize the tubing within the graft.

* * * * *